United States Patent [19]

Groopman et al.

[11] Patent Number: 4,859,611
[45] Date of Patent: * Aug. 22, 1989

[54] AFFINITY COLUMN AND PROCESS FOR DETECTION OF LOW MOLECULAR WEIGHT TOXIC SUBSTANCES

[75] Inventors: John D. Groopman, Lynnfield; Gerald N. Wogan, Belmont; Frederick G. Bargoot, Wellesley; Christopher Ferrari, Marlborough, all of Mass.

[73] Assignees: Massachusetts Institute of Technology, Cambridge; Boston University, Boston, both of Mass.

[*] Notice: The portion of the term of this patent subsequent to Apr. 4, 2006 has been disclaimed.

[21] Appl. No.: 820,388

[22] Filed: Jan. 21, 1986

Related U.S. Application Data

[63] Continuation-in-part of Ser. No. 706,984, Feb. 28, 1985, and a continuation-in-part of Ser. No. 706,983, Feb. 28, 1985.

[51] Int. Cl.[4] .................. G01N 33/543; G01N 33/577
[52] U.S. Cl. ..................................... 436/518; 436/513; 436/548; 436/815; 436/824; 436/825
[58] Field of Search .................. 422/69, 70; 436/513, 436/518, 529, 807, 815, 824, 825, 172, 548; 530/413

[56] References Cited

U.S. PATENT DOCUMENTS

| | | | |
|---|---|---|---|
| 4,181,853 | 1/1980 | Abu-Shumays et al. | 436/172 |
| 4,285,698 | 8/1981 | Otto et al. | 436/172 |

FOREIGN PATENT DOCUMENTS

| | | |
|---|---|---|
| 8102899 | 10/1981 | PCT Int'l Appl. |
| 8302160 | 6/1983 | PCT Int'l Appl. |
| 8303678 | 10/1983 | PCT Int'l Appl. |

OTHER PUBLICATIONS

J. A. Gordon et al., *Biochemistry*, 2, 47–57, 1963.
J. D. Groopman et al., *Proc. Natl. Acad. Sc., USA* 81, 7728–7731, 1984.
A. Haugen et al., *Proc. Natl. Acad. Sci USA*, 78, 4124–4127, 1981.
S. Wu et al, *Zhunghua Zhongliu Zazhi*, 5, 81–84, 1983.

*Primary Examiner*—Robert J. Warden
*Assistant Examiner*—David A. Saunders
*Attorney, Agent, or Firm*—Birch, Stewart, Kolasch & Birch

[57] ABSTRACT

An affinity matrix and a method for the detection of low molecular weight compositions such as aflatoxins are provided utilizing specific monoclonal IgM antibody having an affinity constant not less than about $1 \times 10^9$ liters per mole. Methods for the preparation and use of such affinity matrices are also given. The detection is rapid, accurate, reproducible, and allows for quantitative recovery of the composition of interest.

26 Claims, 3 Drawing Sheets

AFFINITY COLUMN AND PROCESS FOR DETECTION OF LOW MOLECULAR WEIGHT TOXIC SUBSTANCES

RESEARCH SUPPORT

The investigations reported herein were supported by a grant from the National Institutes of Health and American Cancer Society, Massachusetts Division.

CROSS-REFERENCE TO RELATED APPLICATIONS

This application is a continuation-in-part application of co-pending application Nos. 706,983 and 706,984, both filed on Feb. 28, 1985.

FIELD OF THE INVENTION

The invention is concerned with non-invasive immunological screening procedures for assessing the exposure of humans and animals to environmentally occurring toxins and is particularly directed to immunological compositions and processes for the detection of mutagens and carcinogens frequently encountered in many areas of the world.

BACKGROUND OF THE INVENTION

The incidence and effect of exposure to toxic substances by humans and other animals via food, water, and air is of critical importance to our survival. Within the general class of toxic substances, the detection of small molecular weight (1,000 daltons or less) mutagens and/or carcinogens such as aflatoxins, fluoranthene, nitropyrene, nitrofluoranthene, nitrochrysene, and aminobiphenyls have become especially important. In particular, non-invasive screening procedures for assessing the exposure of humans to substances such as aflatoxins require the ability to quantify both the toxin and its metabolites, especially covalent adducts formed with DNA and proteins, in body fluids such as serum and urine.

Aflatoxins are a typical example of the toxic and carcinogenic compounds within this class. Aflatoxins are secondary fungal metabolites, mycotoxins, which are produced by *Aspergillus flavus* and *Aspergillus parasiticus* and are structurally a group of substituted coumarins containing a fused dihydrofurofuran moiety. Aflatoxins occur naturally in peanuts, peanut meal, cottonseed meal, corn, dried chili peppers and the like; however the growth of the mold itself does not predict the presence or levels of the toxin because the yield of aflatoxin depends on growth conditions as well as the genetic requirements of the species. A variety of aflatoxins—types $B_1$, $B_2$, $G_1$, $G_2$, $M_1$ and $M_2$—have been isolated and characterized. Aflatoxin $B_1$ (hereinafter "$AFB_1$") is the most biologically potent of these compounds and has been shown to be toxic, mutagenic and carcinogenic in many animal species. This mycotoxin is a frequent contaminant of the human food supply in many areas of the world and is statistically associated with increased incidence of human liver cancer in Asia and Africa in particular [Busby et al., in *Food-Born Infections and Intoxications* (Riemann and Bryan, Editors) Second Edition, Academic Press, Inc., 1979, pp. 519–610; Wogan, G. N. *Methods Cancer Res.* 7:309–344 (1973)].

$AFB_1$ also forms covalently linked adducts with guanine in DNA after oxidative metabolism to a highly reactive 2,3-exo-epoxide, the major adduct product being 2,3-dihydro-2-($N^7$-guanyl)-3-hydroxy-aflatoxin $B_1$ (hereinafter identified as "$AFB_1$-$N^7$-Gua") [Lin et al., *Cancer Res.* 37:4430–4438 (1977); Essigman et al., *Proc. Natl. Acad. Sci. U.S.A.* 74:1870–1874 (1977); Martin et al., *Nature* (London) 267:863–865 (1977)]. The $AFB_1$-$N^7$-Gua adduct and its putative derivatives [2,3-dihydro-2-($N^5$-formyl-2', 5', 6'-triamino-4'-oxo' $N^5$-pyrimidyl)-3-hydroxy-aflatoxin $B_1$] (hereinafter "AF-$N^7$-Gua") have been identified in a wide variety of tissues and systems such as rat liver in vivo, cultured human bronchus and colon, and human lung cells in culture after acute or chronic administration [Haugen et al., *Proc. Natl. Acad. Sci. U.S.A.* 78:4124–4127 (1981)].

Some investigations regarding quantitation of aflatoxin $B_1$ and its metabolites including its DNA adduct have been conducted using immunological techniques and monoclonal antibodies [Hertzog et al., *Carcinogensis* 3:825–828 (1982); Groopman et al., *Cancer Res.* 42:3120–3124 (1982); Haugen et al., *Proc. Natl. Acad. Sci. U.S.A.* 78:4124–4127 (1981)]. Similar research has been conducted utilizing immunological techniques and reagents for other low molecular weight toxins found in our environment [Johnson et al., *J. Analyt. Toxicol.* 4:86–90 (1980); Sizaret et al., *J.N.C.I.* 69:1375–1381 (1982); Hu et al., *J. Food Prot.* 47:126–127 (1984); and Chu, *J. Food Prot.* 47:562–569 (1984)]. Nevertheless, insofar as is presently known, the development of a general non-invasive screening procedure for assessing the exposure of humans and animals to such environmentally occurring carcinogens has not been achieved.

SUMMARY OF THE INVENTION

The present invention comprises two distinct parts, each of which represents a major advance and contribution to the invention as a whole. One part of the invention is an affinity matrix material for the detection of a toxic substance such as aflatoxin $B_1$ in a test sample comprising a solid phase sorbent material and high affinity IgM antibody specific for the toxic substance, the IgM antibody being bound to the sorbent material. This aspect of the invention provides a novel and widely useful method for purifying samples for testing of toxins by use of a specific monoclonal antibody bound to a sorbent material.

In addition, the invention comprises a method for detecting a low molecular weight substance such as aflatoxin $B_1$ in a fluid sample comprising the steps of preparing an affinity matrix comprised of a homogenous, high affinity IgM antibody specific for the toxic substance of interest, the antibody being immobilized onto a solid phase sorbent material; combining the sample with the affinity matrix such that the substance in the sample is retained by the IgM antibodies; adding a releasing agent to the affinity matrix; and detecting the presence of the toxic substance in the effluent.

DETAILED DESCRIPTION OF THE DRAWING

The present invention may be more fully and easily understood when taken in conjunction with the accompanying drawing, in which.

DETAILED DESCRIPTION OF THE PREFERRED EMBODIMENTS

Figure 1:
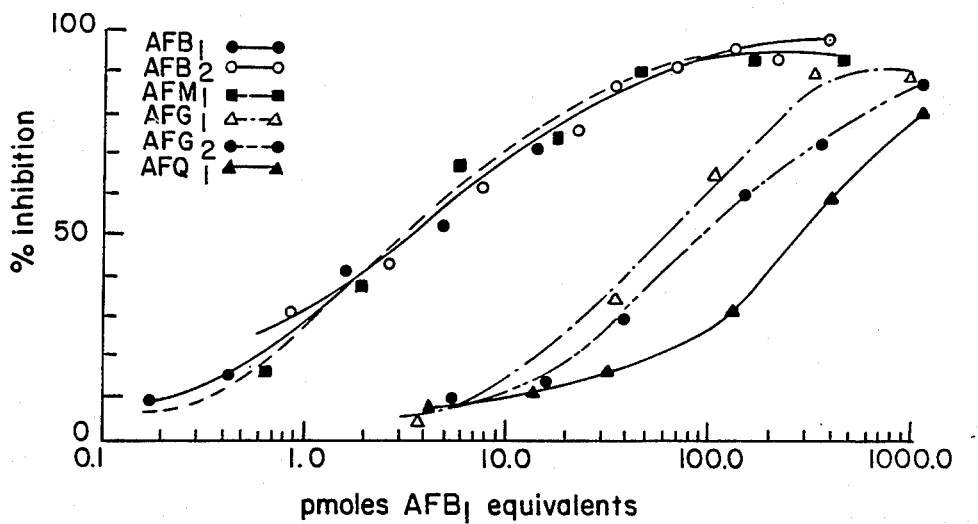
FIG. 1 is a graph illustrating a competitive radioimmunoassay using $^3H$-$AFB_1$ tracer and a variety of aflatoxins to measure the specificity of IgM antibody.
Figure 2:
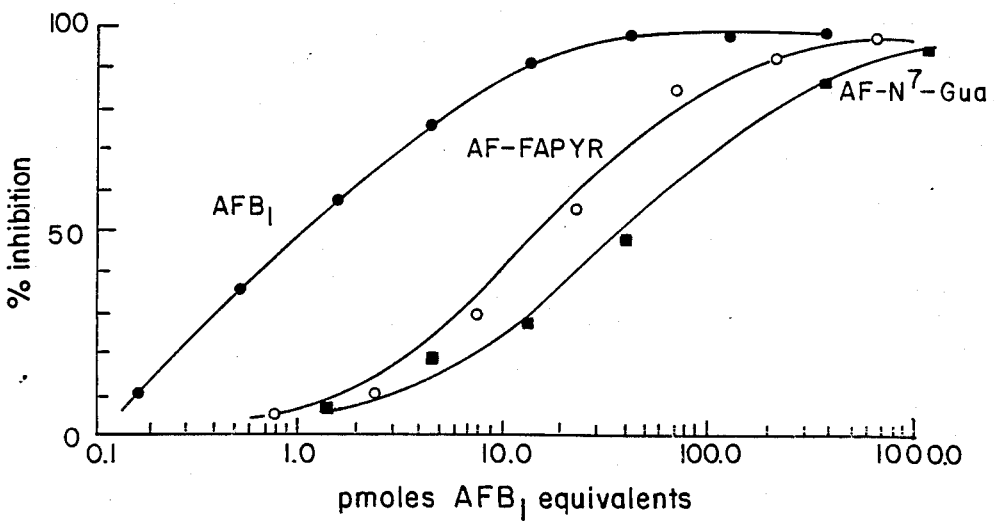
FIG. 2 is a graph illustrating a competitive radioimmunoassay using $^3H$-$AFB_1$ tracer in combination with aflatoxin $B_1$ and the major metabolic aflatoxin-DNA adducts using the IgM antibody.
Figure 3:
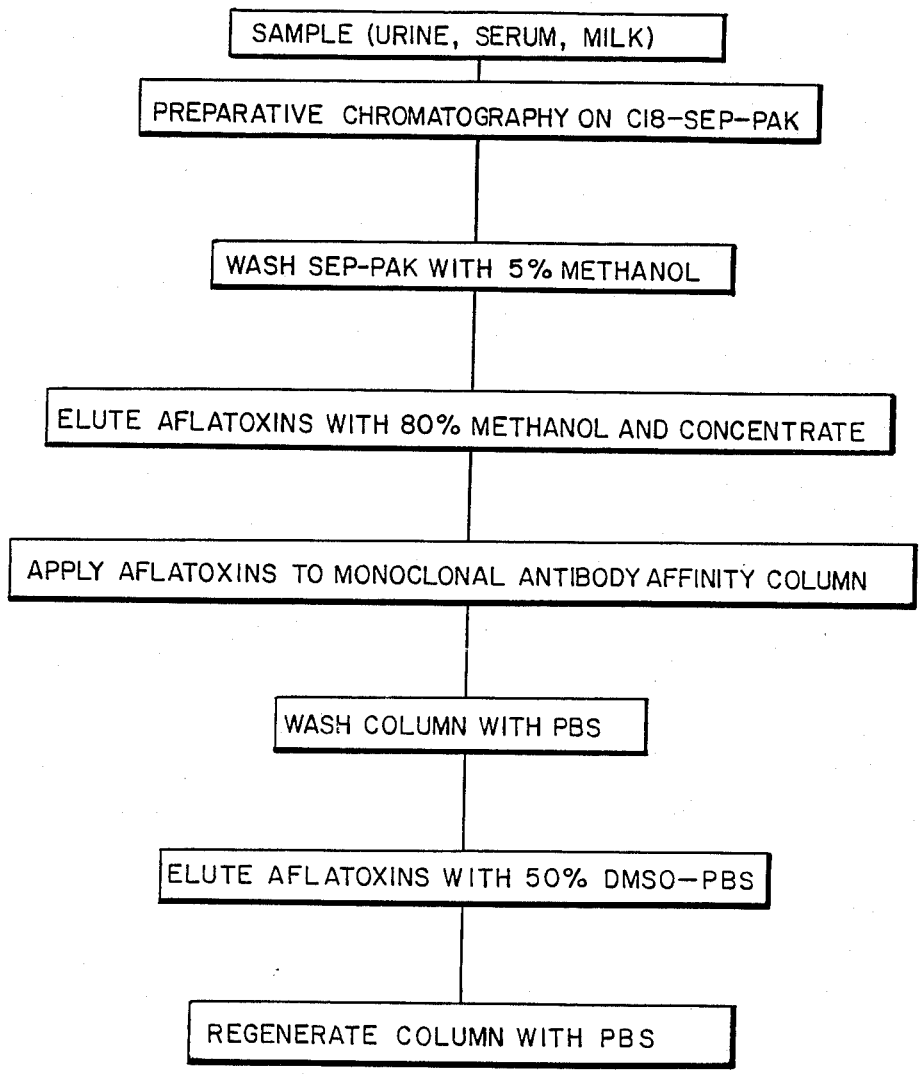
FIG. 3 is a schematic flow outline for the detection and isolation of toxins in general.

The present invention is useful for the detection and isolation of toxic substances generally when they present two critical characteristics: first, the toxic substance has a molecular weight not greater than about 1000 daltons; second, that the toxic substance, either alone or in combination with other compounds, is able to induce an immunological response in vivo when introduced into an animal subject.

The first requirement, a molecular weight not greater than about 1000 daltons, is easily determinable for any toxic substance. The term "toxic substance" as used herein includes all compounds which have been shown to be harmful, hazardous, or destructive, either by in vitro tests or in vivo determinations (including epidemological studies). Most notable are those compounds shown to be mutagenic, genotoxic, and/or carcinogenic as these terms are used and recognized in this art.

The second characteristic, the ability of the toxic substance to induce an immunological response after introduction into a test animal in vivo, relies on its ability primarily (but not exclusively) to induce antibody formation. It is recognized that often the production of antibodies either precedes or is subsequent to other immunological responses and that the ability to induce antibody production is dependent upon methods for the preparation and introduction of the antigen (or hapten) which directly affect the quantitative and qualitative antibody response. For this reason, so long as some type of immunological response is observed, it is understood and accepted that production of specific antibodies can be achieved using the techniques and manipulations presently known in this art.

The invention therefore applies generally to all toxic substances which meet the two requisite criteria. Specifically included within this class of compounds are aflatoxins (regardless of designation) and also those polynuclear aromatic hydrocarbons exemplified by fluoranthene, nitropyrene, nitrosopyrene, nitrofluoranthene, nitrochrysene, and aminobiphenyls (and their derivatives). This general category of aromatic hydrocarbons and each of the specific examples identified are recognized immunogens and are mutagenic/carcinogenic in nature. The invention is particularly useful for studies of aflatoxin $B_1$ and aflatoxin $M_1$. An entire listing of toxic substances which are also immunogens is extensive, varied in chemical composition and structure, and expanding in view of the ever increasing list compiled by the U.S. Dept. of Health and Human Services. In view of this, a true and complete listing is neither possible nor desirable and will not be attempted here. Instead a representative example, aflatoxin $B_1$, will be the toxic substance of choice which is described for use and detection by the present invention. It is expressly understood, however, that the present invention is not limited to this working example nor to those other toxic substances specifically identified above but rather is suitable instead generally for the entire class of toxic substances which meet the two essential requirements.

In view of aflatoxin being the descriptive example herein for all toxic substances of interest as a class and to promote clarity and a complete understanding of the invention in all its component parts, the detailed description will describe each part of the invention independently in separate sections. It will be recognized also that substantial portions of the detailed description relating to the preparation of hybridomas and the production of high affinity IgM antibodies are identical to and shared in common with culture deposit ATCC No. HB8719 and the copending patent application of Groopman, et al., Ser. No. 706,983 filed on Feb. 28, 1985.

I. Preparation of Aflatoxin Immunogen

The preferred immunogen is a composition in which aflatoxin $B_1$ has been conjugated to bovine gamma globulin (hereinafter "BGG"). Initially, BGG (commercial grade) was dissolved in phosphate buffered saline (hereinafter "PBS"), pH 7.0 at a concentration of 10 milligrams per milliliter (hereinafter "mg/ml"). The aflatoxin $B_1$ (hereinafter "$AFB_1$") was conjugated to BGG using a modification of the procedure employing M-chloroperoxybenzoic acid [Martin et al., *Nature London* 267:863–865 (1977)]. Typically one milligram (hereinafter "mg") of $AFB_1$ (3.2 $\mu$moles) was dissolved in 2.0 ml of methylene chloride and added to a 5 molar excess of M-chloroperoxybenzoic acid (mCPBA) which had been previously dissolved in 2.0 ml of methylene chloride. The BGG in PBS buffer solution was added to this reaction mixture to produce a 5 molar excess of aflatoxin relative to the protein content. The reaction mixture was vigorously stirred overnight at ambient temperature and the reaction terminated subsequently by centrifugation at 2,000 times gravity for 20 minutes. The aqueous ephiphase (supernatant) containing the modified BGG protein was then extensively dialyzed against PBS at pH 7.4. The level of modification of the globulin protein was quantified by measuring the absorbance at 362 nanometers, using a molar extinction coefficient of 18,000. The reaction product of such a preparation $AFB_1$-BGG, demonstrated an average of 40–50 $AFB_1$ residues to be bound per molecule per BGG.

It should be noted that $AFB_1$ may be conjugated to other carriers to form the immunogen using the procedure described above. For example, the preparation of $AFB_1$ coupled to bovine serum albumin (hereinafter "BSA") is a useful alternative; the average level of binding the $AFB_1$ to bovine serum albumin, however, is usually only 20–30 molecules of alfatoxin per molecule of BSA. Other useful carriers may be combined with $AFB_1$ to form a conjugate using reaction methodologies presently known in the art. Exemplifying such conjugates are the following: $AFB_1$- BGG (mCPBA); single strand $AFB_1$- DNA - meBSA; $AFB_1$-$N^7$-Gua-BGG-PABA (para amino benzoic acid); $AFB_1$-carboxymethyloxime-KLH (Kehole Limpet Hemocyanin); and $AFB_1$-poly Gua-BGG.

II. Immunization of Mice

Female BALB/By CJ (Jackson Labs), approximately 16 weeks of age, were immunized with $AFB_1$-BGG immunogen which had been dissolved in PBS and emulsified with an equal volume of complete Freund's adjuvant. Using two groups of five mice each, immunization was performed by intraperitoneal injection of 37.5 $\mu$g of $AFB_1$-BGG (with adjuvant) or 12 $\mu$g $AFB_1$-BGG (with adjuvant) in a final volume of 0.2 ml PBS. At 5 weeks and 9 weeks post initial injection, each mouse received an identical quantity of $AFB_1$-BGG emulsified with incomplete Freund's adjuvant. Approximately 10 days after the second injection, serum samples were taken from each mouse via tail bleeding and were assayed for anti-aflatoxin antibody activity by ELISA immunoassay determination. For those mice showing the presence of specific antibody in their serum, each was given a final immunization of the identical $AFB_1$-BGG again in 0.1 ml of PBS injected into the tail vein 3 days prior to sacrifice of the animal.

The ELISA immunoassay alo was used to determine the presence of specific antibodies against $AFB_1$ in mouse sera (and subsequently to identify specific hybridomas); these assays were modifications of methods previously described in the art [Haugen et al., *Proc. Natl. Acad. Sci. U.S.A.* 78:4124–4127 (1981); Groopman et al., *Cancer Res.* 42:3120–3124 (1982)]. Briefly summarizing the procedure, $AFB_1$-BSA was dissolved in PBS at a concentration of 2.0 µg/ml and 50 µl of this fluid mixture was added to each well of a polyvinyl microtiter plate and allowed to incubate for 2–4 hours at ambient temperature. Other wells in the microtiter plate received 50 µl of BSA in PBS at a concentration of 2 µg/ml and served as controls. The fluid in each well was then aspirated and each well washed 3 times with tap water. Subsequently each well received a PBS solution containing either 0.2% BSA or 0.2% gelatin (type IV, Sigma) and the plates were allowed to incubate for an additional hour at ambient temperature. This procedure was designed to limit non-specific binding of antibodies. The plates were then washed in tap water and 50 µl aliquots mouse serum samples (or hybridoma medium) added to each well. To titer the mouse sera, dilutions in PBS containing 10% fetal calf serum were prepared over a range from 1:50–3:50,000 in continuing three-fold dilutions. When using hybridoma media, 50 µl aliquots were used without dilution. In either case, the microtiter plates were then incubated for 90 minutes at 37° C., after which they were thoroughly washed with tap water. Specific antibodies that became bound to the surface of each well were detected by adding 50 µl of a 1:200 dilution of rat anti-mouse kappa antibody coupled to alkaline phosphatase to each well followed by incubation of 4 hours at room temperature or incubation overnight at 4° C. The wells in each plate were then rewashed with tap water. 100 µl per well of 1.0 mg/ml p-nitrophenyl phosphate solution (Sigma) prepared in 0.1M diethanolamine buffer, pH 9.8 then was added and allowed to react for 1–2 hours. Quantitative measurement of the p-nitrophenol reaction product was performed by measuring the absorbance of the assay well at 405 nanometers using a microtiter plate reader (Dynatech Labs).

The isotypes of the monoclonal antibodies (that is the determination and identification of different antibody heavy chain class) were determined in a non-competitive ELISA methodology using a commercially purchased kit for mouse immunoglobulin subtype identification (Boeringer-Mannheim Company).

III. Preparation of Hybridomas and Isolation of Monoclonal Antibody Producing Cells The female BALB/By CJ mice previously immunized with $AFB_1$-BGG in complete Freund's adjuvant were tested for production of significant anti-aflatoxin $B_1$ serum titers using the non-competitive ELISA methodology as described above. Those mice showing high titers were sacrificed and hybridomas prepared following the procedures previously described in Marshak-Rothstein et al., *J. Immun.,* 122:2491–2497 (1979). The myeloma cell line used for cell fusion were SP2/0 cells which were maintained Dulbecco's Modified Eagles medium (hereinafter "DME" medium) supplemented with 20% (volume/volume) fetal calf serum, 580 micrograms per ml (hereinafter "μg/ml") glutamine, 10 units/ml penicillin, 100 μg/ml streptomycin, and non-essential amino acids (Gibco). The mice were sacrificed and spleen cell suspensions prepared using Hanks' balance salt solution buffered with 0.01M phosphate, pH 7.2 (hereinafter "HPBS").

The spleen cells from these mice were fused with SP2/0 myeloma cells using a modification of the Gefter et al. procedure [*Somatic Cell Genet.* 3:321 (1977)]. Unless stated otherwise, all centrifugations were performed at 700 times gravity for 5 minutes at room temperature. Preferably, $5\times10^6$ SP2/0 myeloma cells and $5\times10^7$ immune spleen cells were combined in a round bottom plastic tube, centrifuged, resuspended in 10 ml of serum free DME medium and centrifuged again. The supernatant was carefully discarded and the centrifuge tube tapped sharply to disperse the residual cell pellet. The cells were then exposed to 0.5 ml of a 30% (volume/volume) solution of polyethylene glycol 1000 (Baker Chemical Company) in serum free DME for 6 minutes. During this 6 minute period, the cell suspension was gently centrifuged (150× gravity for 3 minutes). 4.0 ml of serum free DME was then added to the cell pellet and the cells again resuspended by tapping the tube. The contents of the tube were transferred to 100×17 mm Petri dishes and cultured in DME medium containing 20% fetal calf serum for 1 day. The cells were then centrifuged again and resuspended in growth medium containing hypoxanthine, aminopterin and thymidine (hereinafter "HAT medium"). 0.1 ml aliquots of the cells were then distributed into the wells of flat bottom microtiter dishes, each aliquot containing approximately $10^5$ SP2/0 l cells. After one week's incubation, 0.05 ml of growth medium containing only hypoxanthine and thymidine (hereinafter "HT medium") was added to each well. Cultures were screened for specific anti-$AFB_1$ antibody activity two weeks post fusion using the ELISA immunoassay technique described earlier.

Hybridomas secreting IgM antibodies of high affinity specific for $AFB_1$ were grown as ascites tumor cells in BALB/C mice which had been previously injected with 0.5 ml pristane (Aldrich). The hybridomas growing within the mice produced large quantities of specific IgM antibodies which were harvested and collected as ascites fluid from each mouse before it died. The collected fluid from these animals was pooled and either used directly in the immunoassays or further purified by saturated ammonium sulfate precipitation and dialysis against PBS. Gross pathological examination showed that all mice died as a result of widespread tumor invasion—that is growth of the injected hybridoma cells.

Some of the monoclonal antibodies obtained by this method were shown to be a high affinity IgM antibodies having specificity for the $AFB_1$ molecule. Values for the affinity constant for this antibody were determined to be $8\times10^8$ and $1\times10^9$ liters per mole by Scatchard plot analysis and by the method of Muller [*J. Immunol. Meth.,* 34:345–352 (1980)]. The values were derived from data obtained following a competitive RIA procedure as follows:

The assay routinely employed 300 microliter (hereinafter "μl") total volume of which 100 μl consisted of [$^3$H]-aflatoxin $B_1$ tracer (specific activity 3.4 Ci/mmol) purchased from Moravek Biochemicals. The tracer concentrate was diluted in 1% normal mouse serum containing 0.1% BSA in PBS to a level of about 20,200 cpm/100 μl. The monoclonal antibody was diluted to a concentration which precipitated 30–50% of the aflatoxin $B_1$ tracer. The antibody was added to the reaction mixture in 100 μl aliquots which contain 10% fetal calf serum in PBS. The test sample, consisting of non-radiolabelled aflatoxin $B_1$ or its metabolites including the major aflatoxin $B_1$-DNA adducts AF-$N^7$-Gua and AF-FAPyr, were added to the tube in 100 μl volumes. The reaction mixture was incubated at ambient temperature for two hours after which the mixture was brought to a 1.0 ml volume with PBS. An equal volume of ice cold saturated ammonium sulfate solution was then added after which the sample was mixed and allowed to stand on ice for 15 minutes. The sample was then centrifuged for 15 minutes at 2000× gravity and the percent of inhibition in the reaction determined using the Muller methodology.

The specificity of the IgM antibody for $AFB_1$ and its metabolites are shown in FIGS. 1 and 2. It should be noted that these results were obtained using purified IgM antibody of high affinity which was initially fractionated by precipitation with saturated ammonium sulfate followed by dialysis against PBS. The antibody was then purified by high pressure liquid chromatography in a steric exclusion which took advantage of the high molecular weight (900,000 daltons) of the IgM antibody for its separation and isolation. It is the characteristics and properties of this purified IgM antibody whose specificity and high affinity constants were then utilized as described herein. Using the competitive RIA methodology, The 50% inhibition levels for aflatoxin $B_1$, aflatoxin $B_2$ and aflatoxin $M_1$ were found to be 3.0 picomoles whereas those for aflatoxin $G_1$, aflatoxin $G_2$, and aflatoxin $Q_1$ were 60.0, 84.0, and 275.0 picomoles respectively. The data shown in FIG. 2 identifies the specificity and 50% inhibition point for the IgM antibody for aflatoxin $B_1$ and the two major aflatoxin-DNA adducts, AF-FAPyr and AF-$N^7$-Gua. The 50% inhibition values were 3.0, 24.0, and 89.0 pmoles respectively. The data therefore indicates that this IgM antibody is approximately four times more sensitive in detecting the AF-FAPyr adduct than the AF-$N^7$-Gua adduct.

IV. Affinity Matrix Comprising Immobilized Anti-$AFB_1$ IgM Monoclonal Antibody An affinity matrix material was prepared using this purified IgM monoclonal antibody following the procedures described by Pharmacia Fine Chemicals. Sufficient (2.0 mg) monoclonal antibody was dissolved in coupling buffer comprising 0.1M $NaHCO_3$, pH 8.3 and 0.5M NaCl to form a 1.0 mg/ml solution. This antibody solution was added to 2.5 g of cyanogen bromide activated Sepharose-4B (Sigma) which had been incubated previously in 8.0 ml of 0.001M HCl overnight. After the Sepharose and antibody solution were allowed to react for 1 hour, the unbound sites of the antibody bound gel were blocked by incubating the solid phase sorbant material with 1.0M ethanolamine, pH 8.5 for 1 hour. The combination of the IgM antibody immobilized onto the solid phase sorbant material formed an affinity matrix which then was used in volumes of from 1–2 ml.

Although the preferred solid phase sorbant material is the activated Sepharose 4B gel, it is recognized that many other materials may be substituted as the solid phase material. These include other agarose gel compositions, dextrans, carbon and silicon granular preparations and the like, including glass plates. Similarly, methods for immobilizing the high affinity IgM antibody onto each of these different chemical compositions are known and described in the art. For this reason, the preparation of a solid phase sorbant material which is then coupled to the high affinity IgM antibody as described herein in any form, concentration, or configuration is deemed to be within the scope of the present invention.

V. Methodology for Detecting and Isolating Aflatoxins in a Fluid Sample

The methodology for detecting aflatoxins and aflatoxin-DNA adducts in a test sample is an affinity chromatography technique comprising the following steps: Preparing an affinity matrix comprising a homogenous, high affinity IgM antibody specific for the aflatoxin or aflatoxin-DNA adduct of interest which has been immobilized onto a solid phase sorbent material; combining the test sample with the affinity matrix such that those aflatoxins as are present in the test sample become bound to and are retained by the IgM antibodies of the affinity matrix; adding a releasing agent to the affinity matrix for the release of the aflatoxin from the IgM antibodies, this releasing agent comprising at least a 50% (v/v) aqueous solution of a compound selected from the group consisting of dimethyl sulfoxide, dimethyl formamide and dimethyl acetamide; and identifying the presence of the aflatoxin in the effluent collected from the affinity matrix.

A critical characteristic of the anti-aflatoxin IgM monoclonal antibodies is not only its specificity for this $AFB_1$ antigen but also its high affinity constant (at least about $1\times10^8$, and preferably at least about $1\times10^9$, liters per mole) which requires the use of unique releasing agents for the detachment of the aflatoxin of interest after it has become bound to the covalently linked antibody in the affinity column. This is demonstrated by the following examples which identify not only the ability of the antibody bound sorbant material to bind the aflatoxin of interest but also to indicate the inability of releasing agents and eluants known in the art to selectively detach and release the aflatoxin after it has become bound within the affinity column.

EXAMPLE 1

Initial experiments were performed to determine the ability of anti-$AFB_1$ IgM antibody immobilized upon Sepharose 4B as an affinity material to bind aflatoxin $B_1$. In these studies radio-labelled $^3$H-aflatoxin $B_1$ was used at a concentration of 1 nanogram in 10 ml PBS aliquots, a level which would approximate the concentration of aflatoxins expected to be found in the body fluids of humans exposed to contaminated foods. Initially 100 μl of $^3$H-$AFB_1$ tracer in 10.0 ml containing 0.1% BSA, 10 mM $NaN_3$, 0.1 ml normal mouse sera and 3 μl of $^3$H-$AFB_1$ was added to about a 1.0 ml gel bed. The eluant column flow rate was slightly greater than 0.25 ml per minute. About 200 μl of PBS was added to the tracer and transferred to the column by allowing it to run down the column until the top of the affinity matrix was exposed to the air (without allowing the column to dry out). An additional 2.0 ml of PBS was added to wash the tracer through the column and the effluent was collected in a vial as a single fraction (No. 1). In this way approximately 24,486 CPM of tracer material was added to the column and, as each fraction was collected, the effluent analyzed for radio-labelled content by scintillation. Different eluants were then added to the affinity matrix to determine their ability to release the $AFB_1$ tracer. The results are given in Table 1 below.

TABLE I

| Effluent Fraction | Eluant | Volume Used | CPM Per Fraction |
|---|---|---|---|
| | Sample & PBS | 300 ul + 2.0 ml | 2,494 |
| 2 | PBS Wash | 2.0 ml | 287 |
| 3 | 2M KSCN | 3.0 ml | 347 |
| 4 | $PO_4$ buffer/2.64 M NaCl, pH 3.0 | 3.0 ml | 122 |
| 5 | DEA buffers/ 2.64M NaCl, pH 9.9 | 3.0 ml | 36 |
| 6 | $PO_4$ buffer/ 0.14M NaCl, pH 2.0 | 2.0 ml | 38 |
| 7 | 50% DMSO/$PO_4$ Buffer/0.14 NaCl pH 2.0 | 2.0 ml | 23,632 |

Total recovery of radioactivity was 100% within experimental error.

As is evident, about 10% quantitatively of the original tracer was not adsorbed by the affinity matrix initially and was collected in effluent fraction No. 1 prior to the addition of any of the eluants tested. These findings have been attributed to non-specific tritium exchange in the tracer. Subsequent reaction with each eluant listed revealed no substantial release of tracer $AFB_1$ by the IgM antibodies of the matrix in effluent fractions 2-6. It was only after using 50% dimethyl sulfoxide (hereinafter "DMSO") that the bulk (90%) of the $AFB_1$ tracer was released from the affinity matrix. It is also noted that when the DMSO was added to the affinity column, a definite color change within the matrix became visible and the column bed itself became more translucent. When PBS was added to the affinity matrix after the DMSO effluent fraction was collected, the gel bed returned to its original opaque state and normal condition.

It will be appreciated also that the affinity matrix material returned to its original normal condition without damage to or modification of (by denaturation, precipitation, etc.) the IgM antibodies conjugated to the Sepharose gel in any way. This is demonstrated by the continuation of this experiment after the DMSO releasing agent had been added-followed by a washing with PBS.

A second 100 μl quantity of tracer $^3H$-$AFB_1$ dissolved in 200 μl of PBS was then added to the same column which had been previously used to isolate the first sample of $^3H$-$AFB_1$ tracer. The second tracer aliquot was the followed by a rinse of 2.0 ml PBS and the effluent collected as fraction No. 8. A 2.0 ml aliquot of DMSO in PBS was then added and the effluent collected as fraction No. 9. The column was then washed with two additional 2.0 ml PBS aliquots and the effluents collected as fractions 10 and 11. The results are given in Table II below.

TABLE II

| Effluent Fraction No. | Eluant | cpm | % of Original |
|---|---|---|---|
| 8 | PBS | 2,658 | ~10% |
| 9 | 50% DMSO | 14,462 | ~60% |
| 10 | 1st PBS wash | 8,282 | ~30% |
| 11 | 2nd PBS wash | 530 | ~0% |

The second tracer aliquot contained approximately 24,486 cpm as the total radio-label load and it will be noted that approximately 10% of the tracer was not retained by the affinity matrix again. Fraction 9 again indicates that the bulk of the $AFB_1$ tracer was released by the DMSO (about 60%) while the remainder was collected in fraction 10 as the first subsequent PBS washing containing some residual DMSO.

In addition, a variation of this experiment was conducted to show the need for using at least a 50% concentration of DMSO before the releasing effect can be obtained. For this experiment, the 100 μl tracer aliquot of $^3H$-$AFB_1$ contained approximately 27,000–28,000 cpm in total. The 100 μl aliquot of tracer was loaded on to the affinity column followed by an initial washing of 200 μl of PBS to remove the non-retained tracer from the column. The matrix was then washed with increasing concentrations of DMSO in 1.0 ml aliquots. The results are given in Table III below.

TABLE III

| Effluent Fraction No. | Eluant | Volume Used | Effluent cmp |
|---|---|---|---|
| 1 | PBS | 1.0 ml | 455 |
| 2 | PBS | 1.0 ml | 2,271 |
| 3 | 1% DMSO | 1.0 ml | 189 |
| 4 | 1% DMSO | 1.0 ml | 79 |
| 5 | 5% DMSO | 1.0 ml | 45 |
| 6 | 5% DMSO | 1.0 ml | 82 |
| 7 | 10% DMSO | 1.0 ml | 117 |
| 8 | 10% DMSO | 1.0 ml | 92 |
| 9 | 20% DMSO | 1.0 ml | 41 |
| 10 | 20% DMSO | 1.0 ml | 56 |
| 11 | 30% DMSO | 1.0 ml | 86 |
| 12 | 30% DMSO | 1.0 ml | 95 |
| 13 | 40% DMSO | 1.0 ml | 72 |
| 14 | 40% DMSO | 1.0 ml | 50 |
| 15 | 50% DMSO | 1.0 ml | 88 |
| 16 | 50% DMSO | 1.0 ml | 15,682 |
| 17 | PBS | 1.0 ml | 5,966 |
| 18 | PBS | 1.0 ml | 49 |

It is apparent by the results in Table III that there is no substantial release of $^3H$-$AFB_1$ from the affinity matrix prior to using a 50% solution of DMSO. It was found also that concentrations of DMSO greater than 50% did not measurably increase the rate or quantity of $AFB_1$released from the affinity matrix. For this reason, any concentration of DMSO of at least 50% is sufficient for use as the releasing agent in this methodology. Other releasing agents found suitable for use in this methodology were dimethyl formamide and dimethyl acetamide; each of these should be used in a concentration of at least 50% in order to be effective as a releasing agent. The use of these releasing agents, or aprotic solvents in general, permits the affinity matrix or column to be reusable for numerous sample runs. Eluting with such aprotic solvents does not cause deterioration of the matrix material, which may be of importance to industrial applications for the detection and measurement of mycotoxins. Economical use of the process in industrial applications would require a reusable affinity matrix and elution with aprotic solvents, such as DMSO, meets this need.

On the other hand, elution can also be performed with lipophilic solvents, such as methanol and ethanol, in which case the affinity matrix or column will be substantially nonreusable. According to this aspect of the invention, elution is conducted with preferably 50-100% methanol or ethanol, particularly 100%, proceeding similar to the procedure described above, except substituting methanol or ethanol for DMSO.

VI. In Vitro Isolation of Aflatoxin from Human Urine, Serum and Milk

As demonstrated above, the capacity of the IgM antibody affinity matrix to bind $AFB_1$, as determined by radiometric and absorbance technique, was to bind 1.0–1.3 μg of $AFB_1$ from 10 ml of PBS per 1 ml of column bed volume. These parameters may be used to isolate and detect aflatoxins in vitro from human urine, serum and milk samples as follows:

Human serum (10 ml aliquots) or human milk (10 ml aliquots) may be applied directly to the antibody matrix without prior treatment of the sample. In both instances, quantitative binding of aflatoxins in the fluid sample to the antibody matrix occurs which are then quantitatively recovered using a 50% concentration of DMSO as the releasing agent. This has been empirically determined using $^3H$-$AFB_1$ in 1 nanogram concentrations added directly to the serum or milk samples in the manner earlier described. Therefore, when testing either serum or milk test samples, no preparative steps are required for quantitative recovery of the aflatoxin.

Urine samples however require a preparative step involving preparative chromatography to remove interfering materials, e.g. salts, within the sample before isolation and recovery of the aflatoxin can be achieved. This is shown schematically in FIG. 3 in which a Sep-Pak $C_{18}$ cartridge (Waters Associates, Inc.) is preferably used to remove the interfering materials. If the urine sample is first passed through a preparative, low pressure, liquid chromatography cartridge to remove proteins and other interfering materials, 90–95% of the aflatoxins present in human urine samples are consistently and quantitatively recovered using the present methodology.

It should be noted also that the use of high affinity IgM antibody specifically raised against $AFB_1$ is also useful for the detection and recovery of the $AFB_1$-DNA adduct, $AFB_1$-$N^7$-Gua on a quantitative basis. These aflatoxin DNA adduct products can be detected without any preparative step and recovered quantitatively from serum and other bodily fluids. If urine from humans and animals comprise the test sample it is preferred that the preparative step of HPLC through a carbon chromatography cartridge be performed initially before adding the sample to the affinity matrix. In this manner, a quantitative and qualitative method is available to isolate and purify aflatoxin $B_1$ and its metabolites from complex biological samples obtained from environmentally exposed populations. In addition, it also serves as an analytical methodology for the detection of the aflatoxin itself.

From the above, it can be seen that the present invention provides a means for easily and accurately detecting levels of a toxin, particularly aflatoxin, in a sample. An important aspect of the invention is the affinity matrix or column to which is bound the specific monoclonal antibody. The use of such an affinity matrix comprised of antibody immobilized onto a solid phase sorbant provides a means for quick, efficient high purification of samples for testing. Because of the high affinity and selectivity characteristics of the monoclonal antibody, a crude ground extract of a sample can be run through the antibody-matrix column, whereby the toxin of interest will bind to the antibody while all remaining ingredients of the sample extract will pass through. Subsequent elution with an appropriate releasing agent, such as DMSO or methanol, will result in an eluting of the toxin into a collected sample which will contain highly purified toxin in quantitative yields from the original crude sample. Such an efficient one-step purification procedure is an important advance, particularly in the field of assays for toxins.

This important aspect of the invention has broad applications to the detection and measurement of other toxins, particularly mycotoxins, by the use of a matrix or column having bound thereto a monoclonal antibody specific for the toxin of interest. Once the toxin has been purified by means of the antibody-matrix material, detection of the toxin can be made, as desired, by various qualitative or quantitative assay measurement techniques, such as fluorescence, immunoassay, radioimmunoassay, ELISA method, TLC, HPLC, gas chromatography, colorimetric analysis, and the like. Selection of the particular detection method will depend upon a variety of factors, including type of toxin, expected level of toxin and the use for the detected data. In either event, the present invention provides a method utilizing an affinity matrix having bound thereto a monoclonal antibody whereby samples for analysis and detection can be prepared simply and quickly by a single pass through the affinity matrix.

For aflatoxins, one preferred detection method is fluorescence, whereby the purified sample is subjected to UV light (365 nm) and the aflatoxin fluoresces at 425 nm. This type of analysis is particularly preferred because of its easy performance and yet its usefulness in even providing some level of quantitative detection. These fluoresence analysis procedures can be conducting following AOAC methodology (see AOAC Methods, Ch. 26, pp. 414–429 (1980) hereby incorporated by reference).

Because the use of the antibody bound matrix permits such improved one-step purification of a sample containing toxin, the invention is applicable to a variety of samples which could be tested for levels of toxins, including industrial wastes and foods, such as corn, peanuts and the like, as well as body fluids. A general flow diagram for the overall process is set forth below, exemplified by use of a corn sample.

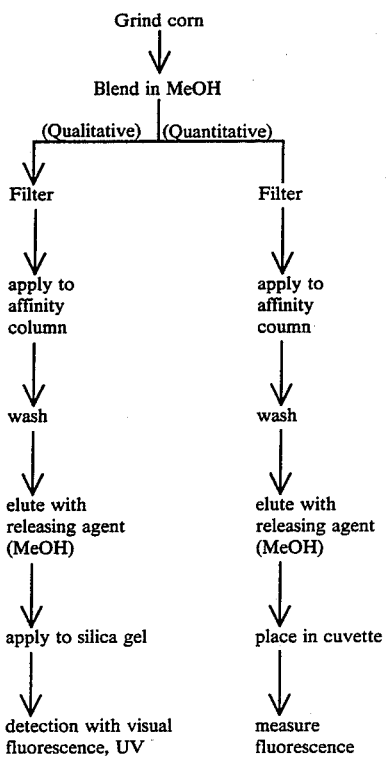

From this flow diagram, it is clear that the important common step resides in purification of the sample by use of the affinity column having the specific monoclonal antibody bound thereto. Once the sample is purified, the toxin level or presence can be qualitatively or quantitatively measured by a variety of means, and all or part or none of the procedure can be automated.

Qualitative Assay

Figure 4:
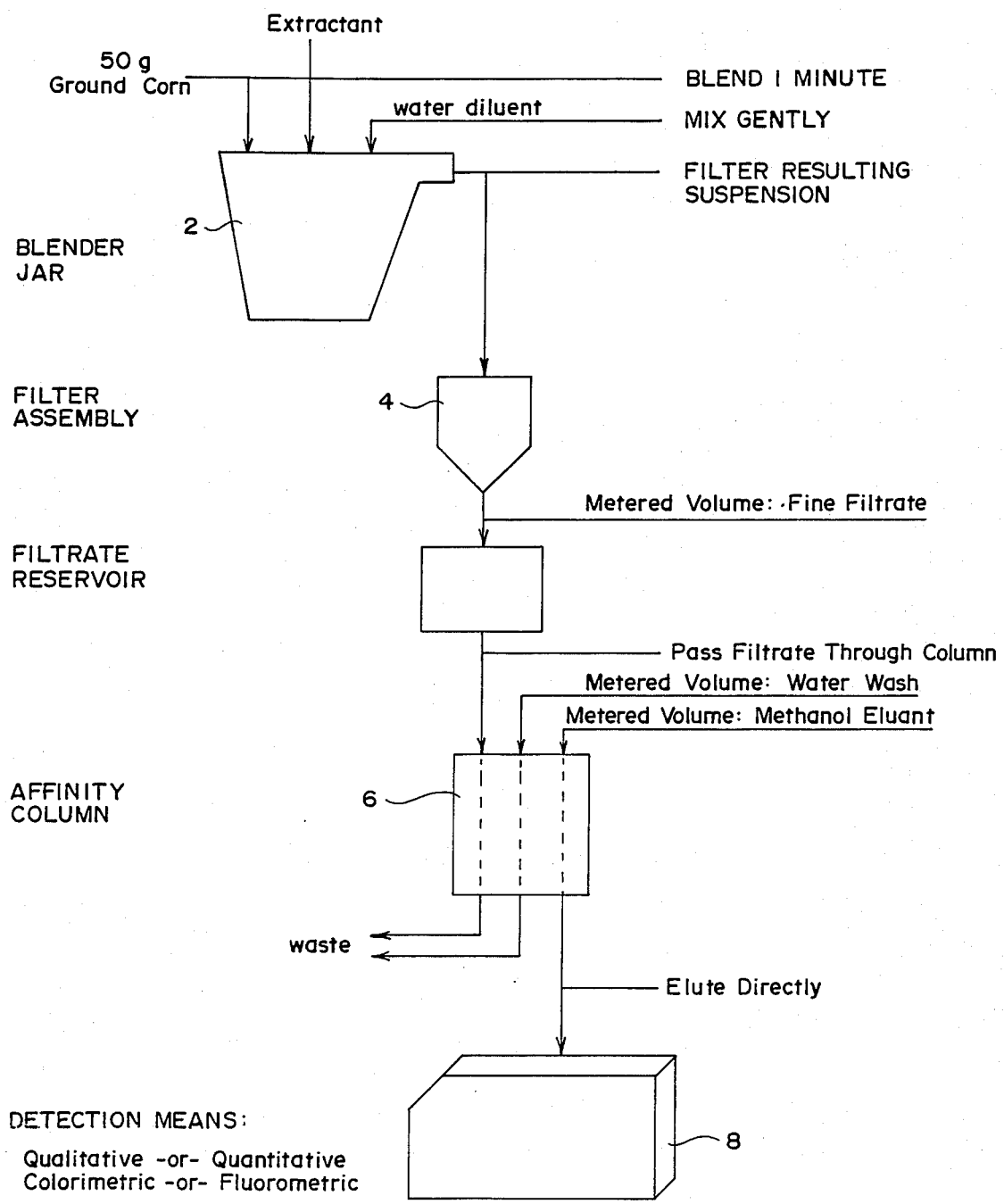
FIG. 4 is a schematic flow outline for an apparatus for automatically conducting an aflatoxin assay procedure.

Toxin levels according to the invention can first of all be measured qualitatively. As a particular example, aflatoxin levels in a corn sample can be detected according to the following process steps:
1. Weigh-out 50 gms of ground corn
2. Place ground corn in blender
3. Add Methanol to blender
4. Blend for 1 minute
5. Add to blended mix Distilled Water and mix
6. Draw extract from blender through a filter
7. Deliver extract through aflatoxin affinity column
8. Deliver Distilled Water through aflatoxin affinity column
9. Deliver Methanol through aflatoxin affinity column (hopefully contained in a syringe) into reaction vessel containing means for fluorescent illumination
10. Remove vessel containing means for fluorescent illumination and place in apparatus for visually determining fluorescence level (not quantitative)
11. Remove and dispose-of vessel Quantitative Assay On the other hand, toxin level can be quantitatively measured according to the following procedure, again as exemplified with aflatoxin measurement in corn:
1. Weigh-out 50 gms of ground corn
2. Place ground corn in blender
3. Add Methanol to blender
4. Blend for 1 minute
5. Add to blended mix Distilled Water and mix
6. Draw extract from blender through a filter
7. Deliver extract through aflatoxin affinity column
8. Deliver Distilled Water through aflatoxin affinity column
9. Deliver Methanol through aflatoxin affinity column into test cuvette contained in measuring apparatus
10. Read results
11. Automated disposal of liquid sample The above qualitative and the quantitative procedures can be performed manually, partially automated or fully automated. FIG. 4 shows an automated system for aflatoxin assays, comprising essentially a blending means 2, a filter means 4, an affinity column 6, an eluent metering and dispensing means and a detection means 8 for either qualitative or quantitative detection of aflatoxin.

The invention is not to be restricted in form nor limited in scope except by the claims appended hereto.

What we claim is:

1. A method for detecting toxins in a test sample, said method comprising:
   preparing a sample believed to contain a toxin;
   placing said sample on an affinity column comprised of a solid phase sorbant material and, immobilized thereon, a monoclonal antibody specific for said toxin;
   eluting said column with a solvent to recover a first eluent, whereby said toxin is retained on said column by said monoclonal antibody and separated from all other ingredients of said sample;
   eluting said column with a releasing agent to recover a second eluent, whereby said toxin is released from said antibody and recovered in said second eluent; and
   subjecting said second eluent to fluorescence measurement by exposing said second eluent to UV light for detection of the presence of said toxin, with the proviso that said second eluent is not subjected to high pressure liquid chromatography or other purification subsequent to recovery from said column.

2. A method according to claim 1, wherein said releasing agent comprises a not less than 50% solution of an aprotic solvent.

3. A method according to claim 2, wherein said aprotic solvent is dimethyl sulfoxide, dimethyl formamide or dimethyl acetamide.

4. A method according to claim 1, wherein said releasing agent comprises a 50–100% solution of a lipophilic solvent.

5. A method according to claim 4, wherein said solvent comprises 100% methanol or 100% ethanol.

6. A method according to claim 5, wherein said toxin is aflatoxin $B_1$ or aflatoxin $M_1$ and said antibody is specific for said aflatoxins with an affinity of at least about $1 \times 10^8$ liters per mole.

7. A method according to claim 6, wherein said second eluent is exposed to UV light at 365 nm for visual detection of the presence of aflatoxin.

8. A method according to claim 6, wherein said second eluent is subjected to quantitative analysis for determining the level of aflatoxin in said sample.

9. A method according to claim 1, wherein said toxin is a mycotoxin having a molecular weight of not more than about 1,000 daltons.

10. A method according to claim 9, wherein said toxin is a member selected from the group consisting of aflatoxins, fluoranthene, nitropyrene, nitrosopyrene, nitrofluoranthene, nitrochrysene, aminobiphenyl, and their respective conjugates and derivatives.

11. A method according to claim 1, wherein said sample is serum, urine or food product.

12. A method according to claim 11, wherein said food product is milk, corn or peanut products.

13. A method for detecting aflatoxins in a test sample, said method comprising:
  placing a sample believed to contain aflatoxin on an affinity column comprised of a solid phase sorbant material and, immobilized thereon, a monoclonal antibody for said aflatoxin;
  eluting said column with a solvent to recover a first eluent, whereby said aflatoxin is retained on said column by said monoclonal antibody and separated from all other ingredients of said sample;
  eluting said column with a releasing agent to recover a second eluent, whereby said aflatoxin is released from said monoclonal antibody and recovered in said second eluent; and
  subjecting said second eluent to fluorescence measurement by exposing said second eluent to UV light for detection of the presence of said aflatoxin, with the proviso that said second eluent is not subjected to high pressure liquid chromatography or other purification subsequent to recovery from said column.

14. A method according to claim 13, wherein said releasing agent comprises a not less than 50% solution of an aprotic solvent.

15. A method according to claim 14, wherein said aprotic solvent is dimethyl sulfoxide, dimethyl formamide or dimethyl acetamide.

16. A method according to claim 13, wherein said releasing agent comprises a 50–100% solution of a lipophilic solvent.

17. A method according to claim 16, wherein said solvent comprises 100% methanol or 100% ethanol.

18. A method according to claim 13, wherein said antibody has an affinity of at least about $1 \times 10^8$ liter per mole for the aflatoxin of interest.

19. A method according to claim 13, wherein said sample comprises serum, urine or food product.

20. A method according to claim 19, wherein said food product is milk, corn or peanut products.

21. A method according to claim 13, wherein said second eluent is exposed to UV light at 365 nm.

22. A method according to claim 13, wherein said second eluent is subjected to quantitative analysis for determining the level of aflatoxin in said sample.

23. A method for detecting aflatoxins in a test sample, said method comprising:
  placing a sample believed to contain aflatoxin on an affinity column comprised of a solid phase sorbant material and, immobilized thereon, a monoclonal antibody for said aflatoxin;
  eluting said column with a solvent to recover a first eluent, whereby said aflatoxins are retained on said column by said antibody and separated from all other ingredients of said sample;
  eluting said column with a releasing agent comprised of ethanol or methanol to recover a second eluent, whereby said aflatoxins are released from said antibody and recovered in said second eluent; and
  subjecting said second eluent to fluorescence measurement by exposing said second eluent to UV light at 365 nm for detection of the presence of aflatoxins, with the proviso that said second eluent is not subjected to high pressure liquid chromatography or other purification subsequent to recovery form said column.

24. A method according to claim 23, wherein said antibody has an affinity of at least about $1 \times 10^8$ liters per mole to said aflatoxins.

25. A method according to claim 23, wherein said sample comprises serum, urine or food product.

26. A method according to claim 25, wherein said food product is milk, corn or peanut products.

* * * * *

UNITED STATES PATENT AND TRADEMARK OFFICE
CERTIFICATE OF CORRECTION

PATENT NO. : 4,859,611

DATED : August 22, 1989

INVENTOR(S) : Groopman et al.

It is certified that error appears in the above-identified patent and that said Letters Patent is hereby corrected as shown below:

ON THE TITLE PAGE

In the category "[75] Inventors:" change

"John D. Groopman, Lynnfield;
Gerald N. Wogan, Belmont;
Frederick G. Bargoot, Wellesley;
Christopher Ferrari, Marlborough,
all of Mass."

to

--John D. Groopman, Lynnfield;
Gerald N. Wogan, Belmont;
Ann Marshak-Rothstein; Newton,
all of Mass.--

Signed and Sealed this

Twenty-eighth Day of July, 1992

*Attest:*

DOUGLAS B. COMER

*Attesting Officer*    Acting Commissioner of Patents and Trademarks